United States Patent [19]

Kusano et al.

[11] Patent Number: 4,634,382
[45] Date of Patent: Jan. 6, 1987

[54] ATTACHMENT FOR DENTAL PROSTHESIS

[75] Inventors: Takae Kusano; Masato Ueno, both of Hiroshima, Japan

[73] Assignees: Molten Corp.; Kabushiki Kaisha Four Brain, both of Hiroshima, Japan

[21] Appl. No.: 740,595

[22] Filed: Jun. 3, 1985

[30] Foreign Application Priority Data

Jun. 7, 1984 [JP] Japan .............................. 59-85375[U]
Jun. 11, 1984 [JP] Japan .............................. 59-87126[U]
Jun. 26, 1984 [JP] Japan .............................. 59-97021[U]
Jun. 26, 1984 [JP] Japan .............................. 59-97022[U]

[51] Int. Cl.$^4$ ............................................. A61C 13/22
[52] U.S. Cl. ..................................................... 433/182
[58] Field of Search ................. 433/180, 181, 182, 183

[56] References Cited

U.S. PATENT DOCUMENTS 4,362,509 12/1982 Sulc ..................................... 433/181
4,488,875 12/1984 Niznick ............................... 433/177
4,571,185 2/1986 Rota .................................... 433/181

Primary Examiner—Robert Peshock
Attorney, Agent, or Firm—Armstrong, Nikaido, Marmelstein & Kubovcik

[57] ABSTRACT

According to the present invention, there is provided for an attachment for a dental prosthesis comprising: (a) a male member made of a rigid material provided at a retentive tooth or a dental root; and (b) a female member provided at the dental prosthesis and facing to the male member, wherein the female member has an elastic part made of an elastic material in order to grip at least an engaging portion of the male member, and the elastic part is formed as one body with an elastic lining layer made of an elastic material and being provided at an inner surface of the dental prosthesis to be in contact with an alveolus ridge. Whereby, the dental prosthesis can be stably and softly supported on the alveolus ridge.

4 Claims, 17 Drawing Figures

ATTACHMENT FOR DENTAL PROSTHESIS

BACKGROUND OF THE INVENTION

The present invention relates to an attachment for a dental prosthesis.

Figure 9:
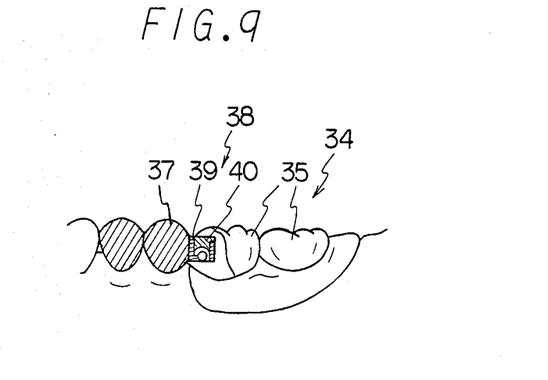
FIG. 9 is a partial sectional view showing a typical conventional Dalbo attachment for a partial dental prosthesis in the state that a partial dental prosthesis having the attachment is set in a mouth of a patient.
Figure 10:
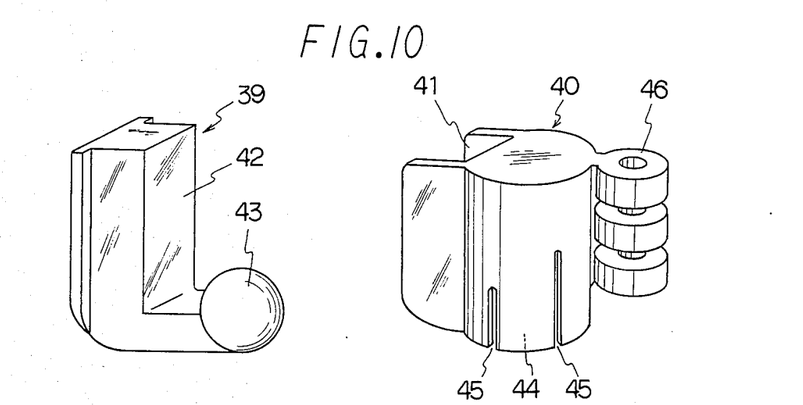
FIG. 10 is an enlarged perspective view showing the attachment in FIG. 9 in the state that a male member and a female member are separated to each other.
Figure 11:
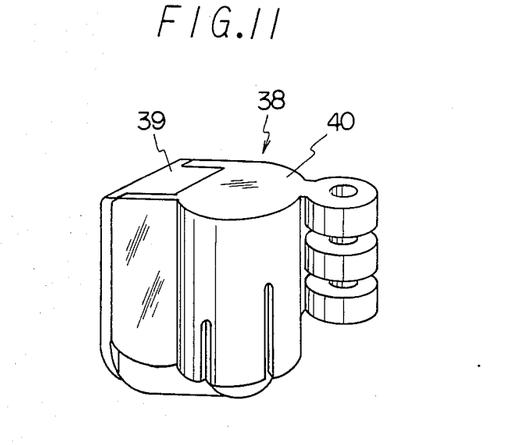
FIG. 11 is an enlarged perspective view showing the attachment in FIG. 9 in the state that the male member and the female member are engaged with each other.

A typical conventional Dalbo attachment for a partial dental prosthesis is shown in FIGS. 9 to 11, which are a partial sectional view (FIG. 9) showing the conventional Dalbo attachment comprising a male and a female in the state that a partial dental prosthesis having the Dalbo attachment is set in a mouth of a patient, an enlarged perspective view (FIG. 10) showing the Dalbo attachment of FIG. 9 in the state that the male and the female are separated to each other, and an enlarged perspective view (FIG. 11) showing the Dalbo attachment of FIG. 9 in the state that the male and the female are engaged with each other, respectively. The Dalbo attachment is described in Etsuro Matsuo, Clinic Concerning Attachment, pages 9 to 11, published on Nov. 15, 1970 by Ishiyaku Shuppan Kabushiki Kaisha. In FIGS. 9 to 11, numeral 34 indicates a partial dental prosthesis. The partial dental prosthesis 34 has artificial teeth 35 and a denture base 36 on which the artificial teeth 35 are held. Numeral 37 indicates a retentive tooth which is a natural tooth covered with a metallic crown. Numeral 38 indicates a Dalbo attachment. The Dalbo attachment 38 has a male member 39 secured to the retentive tooth 37 by soldering and a female member 40 secured to the partial dental prosthesis 34. The male member 39 and the female member 40 are made of Au containing Pt, respectively. As shown in FIG. 10, the male member 39 has a rail 42, an arm extending from the lower end of the rail 42 perpendicular to the longitudinal axis of the rail 42 and a spherical body 43 provided at a free end of the arm. The female member 40 has a groove 41 capable of being slidably in contact with the rail 42, a hole 44 having a circular section of which diameter is smaller than that of spherical body 43 and which can be engaged with the spherical body by receiving the spherical body from lower side, slits 45 (as shown in FIG. 5) longitudinally extended along a wall defining the hole 44 and a fixing element 46 through which the female member 40 is secured to the artificial tooth 35.

In operation of the Dalbo attachment 38, the groove 41 of the female member 40 is made to be in contact with the rail 42 of the male member 39. The female member 40 is slided downwardly in the state that the groove 41 is in contact with the rail 42. Then, the spherical body 43 of the male member 39 is engaged with the circular hole 44. That is to say, the spherical body 43 is fixed into the hole 44 with the elastic gripping force (applied in the direction of a center of the hole 44) of the wall. The elastic gripping force of the female 40 is generated due to the slits 45.

In such a Dalbo attachment, there are problems, as follows:

(1) The attachment of this kind is easy to break, since the mechanical strength of the attachment constituted by precisely processing metallic material is weak. In detail, an occlusal pressure (about 60 kg/cm$^2$) causes a large force which applies to the attachment, so that the attachment is easy to be broken. Further, once the attachment is broken, it is almost impossible to repair. In consideration of the fact that the attachment is made of expensive metal such as Au containing Pt, the repairing cost is very high.

(2) In the above described case, not only the attachment is broken, but also the retentive tooth and the artificial tooth might be broken due to the excessive occlusal pressure.

(3) The work for securing the male and the female (both of them have mm-order-size) to the retentive tooth and the artificial tooth, respectively, requires not only high technique and high skill, but also a long manufacturing time.

(4) It is insanitary to use the above described Dalbo attachment having the cutting lines, since a space is formed by the cutting lines when gripping the spherical body elstically. Therefore, the space is easily filled with dregs remaining in the mouth after eating.

(5) The force for securing the female member 40 to the artificial tooth 35 is weak, since the female member is secured to the artificial tooth substantially only through the element 46.

Figure 12:
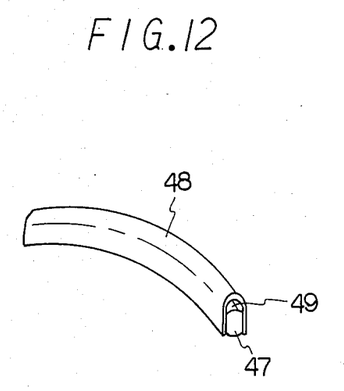
FIG. 12 is a partial perspective view showing a Dolder bar and a sleeve of a conventional bar attachment for a dental prosthesis in the state of engaging with each other.
Figure 13:
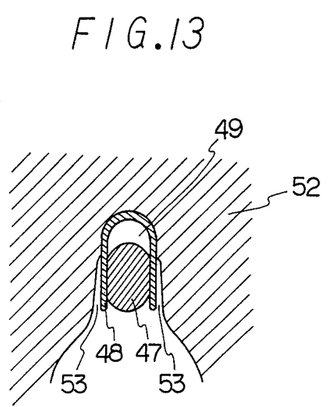
FIG. 13 is a partial sectional view showing the attachment in FIG. 12 in the state that the Dolder bar is engaged with the sleeve.

On the other hand, a bar attachment for a dental prosthesis is well known. Such a bar attachment is described in Etsuro Matsuno, Clinic Concerning Attachment, page 30, published on Nov. 15, 1970 by Ishiyaku Shuppan Kabushiki Kaisha or Japanese unexamined patent application No. 102238/1981. The bar attachment is known as Dolder bar attachment, Ackermann bar attachment and Hader Plastik Reiter. The Dolder bar attachment for the dental prosthesis is shown in FIGS. 12 and 13, which are a partial perspective view showing a Dolder bar and a sleeve of the conventional Dolder bar attachment for a dental prosthesis in the state of engaging with each other and a partial sectional view showing the attachment in FIG. 12 in the state that the Dolder bar is engaged with the sleeve, respectively. In FIG. 12, the Dolder bar attachment comprises a bar 47 having an approximate circular section, for example, an oval section and a sleeve 48 with which the bar 47 is engaged. Numeral 49 is a space provided between the bar 47 and the sleeve 48. The space 48 has an operation to absorb a pressure applied to the attachment. The bar 47 is curved along the shape of an alveolus ridge 4. Both ends of the bar 47 are fixed to dental roots, for example, of canine teeth. The sleeve 48 is provided in a groove formed in an inner surface of the denture base 52 as shown in FIG. 13. Numerals 53, 53 indicate spaces provided between the lower outer surfaces of the sleeve 48 and the corresponding lower inner side surfaces of the groove. The spaces give an elasticity to the sleeve 48. That is to say, when the bar 47 is engaged with the sleeve 48, the sleeve 48 can be widened outwardly. Therefore, the bar 47 is elastically gripped by the force generating when the widened sleeve 48 returns to the original shape.

In such a bar attachment, there are several problems, as follows:

(1) With respect to the Dolder bar attachment or the Ackermann bar attachment, it is necessary that the spaces are provided between the lower outer surfaces of the sleeve and the correponding lower inner side surfaces of the groove in order to give an elasticity to the sleeve. However, dregs existing in the mouth are easy to come into the spaces, so that it is unsanitary to use the attachment in the mouth.

(2) The elasticity of the sleeve becomes unstable, since the sleeve is made of metal. Due to the repeated use, the force that the sleeve elastically grips the bar tends to decrease.

(3) The bar and the sleeve must be correspondingly curved with each other. However, it is very difficult that both of them are precisely formed into the corresponding shapes and are precisely located to each predetermined position. Conventionally, the forming and locating steps are performed by a manual work of the skilled person.

(4) With respect to the Hader Plastik Reiter, the strength is weak, since the sleeve is made of a plastic. Therefore, it is necessary to increase the thickness of the sleeve, but it is difficult to manufacture such a sleeve, further, it is not easy to precisely locate the sleeve to the predetermined position.

(5) With respect to the Dolder bar attachment and Ackermann bar attachment, since the space is provided between the bar and the sleeve so that these attachments have the means for absorbing pressure during a mastication movement, dregs in the mouth unsanitarily tend to come into the space.

Figure 14:
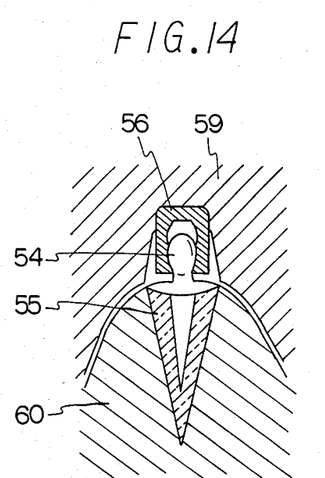
FIG. 14 is a partial sectional view showing a conventional stud attachment for the dental prosthesis in the state that a male member is engaged with a female member.
Figure 15:
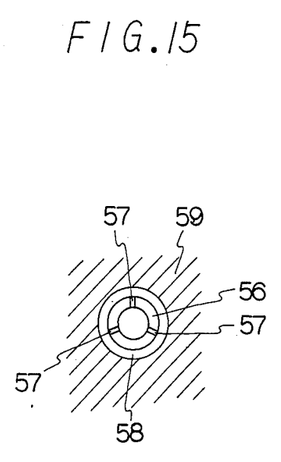
FIG. 15 is a plan view showing an opened end of a female member of the attachment in FIG. 14.

Further, a stud attachment for a dental prosthesis is well known. The stud attachment for the dental prosthesis is shown in FIGS. 14 and 15, which are a partial sectional view showing the conventional stud attachment for the dental prosthesis in the state that a male member is engaged with a female member and a plan view showing an opened end of a female member of the attachment in FIG. 14. Such a stud attachment is described in Etsuro Matsuo, Clinic Concerning Attachment, page 29, published on Nov. 15, 1970 by Ishiyaku, Shuppan Kabushiki Kaisha or Japanese unexamined patent application No. 72911/1980. In FIG. 14 and FIG. 15, numeral 54 indicates a metallic male pin. The male pin 54 is fixed to a surface of a dental root 55 formed by cutting a corona dentis of a natural tooth. Numeral 56 indicates a metallic female member which is engaged with the male pin 54. The female member 56 is formed into a cylindrical body. The cylindrical body is closed at an end and opened at the other end. The closed end side of the cylindrical body is embedded into a hole which is provided in an inner surface of a denture base 59. Then, the closed end side of the cylindrical body is fitted on an corresponding inner peripheral surface of the hole, and the opened end side is apart from the corresponding inner peripheral surface of the hole. That is to say, there is a space between a side surface of the opened end side and the corresponding inner peripheral surface of the hole. At the opened end side of the cylindrical body, the cylindrical body has three cutting lines 57 extending from the opened end in the direction of an axis of the cylindrical body. The inner diameter of the opened end is smaller than the inner diameter of the other portion of the cylindrical body and the maximum diameter of the head portion of the male pin 54. When the male pin 54 is inserted into the female member 56, the inner diameter of the opened end of the female member 56 radially becomes large due to the cutting lines 57. When the male pin 54 is completely engaged with the female member 56, the diameter of the opened end of the female member is a little returned so that the opened end of the female member can grip the male pin.

In such a stud attachment, there are several problems, as follows:

(1) Dregs in a mouth of a patient unsanitarily come into the female member through the cutting lines longitudinally extending from the opened end of the female member, and come into the space between the opened end of female member and the inner peripheral surface of the hole.

(2) Since the female member is made of metal, the gripping force becomes unstable. Due to the repeated mastication movement, the gripping force of the female member tends to reduce.

(3) The work to manufacture such an attachment is performed by the manual work of skilled person, since the female member is made of an expensive dental material such as Au containing Pt and precise manufacturing work is required. Therefore, there are problems in cost and working efficiency.

(4) When the force applied to the dental prosthesis is a force which generated in the direction except occlusal pressure direction, for example, the holizontal direction or the direction rotating around an axis extending from the tongue side to the cheak side, the force is transmitted to the male pin and the dental root through the female member. Therefore, it is feared that the female member, the male pin and the dental tooth are damaged.

An object of the present invention is to provide an attachment for a dental prosthesis which resolve the aforementioned problems of the prior art.

SUMMARY OF THE INVENTION

According to the present invention, there is provided an attachment for a dental prosthesis comprising: (a) a male member made of a rigid material provided at a retentive tooth or a dental root; and (b) a female member provided at the dental prosthesis and facing to the male member, wherein the female member has an elastic part made of an elastic material in order to grip at least an engaging portion of the male, and the elastic part is formed as one body with an elastic lining layer made of an elastic material and being provided at an inner surface of the dental prosthesis to be in contact with an alveolus ridge.

DETAILED DESCRIPTION OF THE INVENTION

Figure 1:
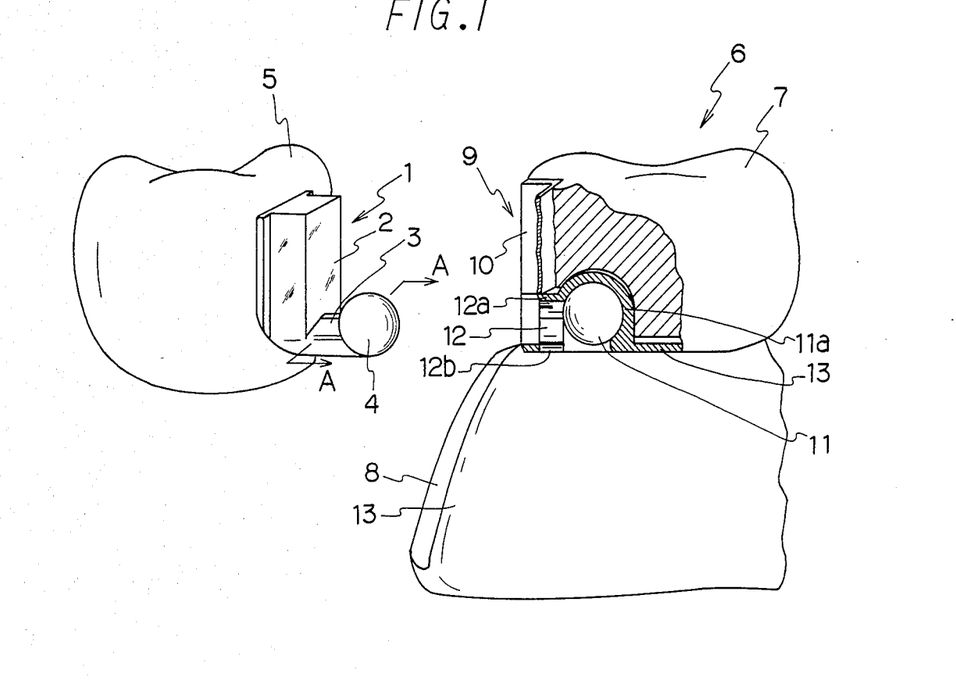
FIG. 1 is a partially cut-away perspective view showing a first embodiment (an improved Dalbo attachment) of an attachment for the dental prosthesis of the present invention.
Figure 2:
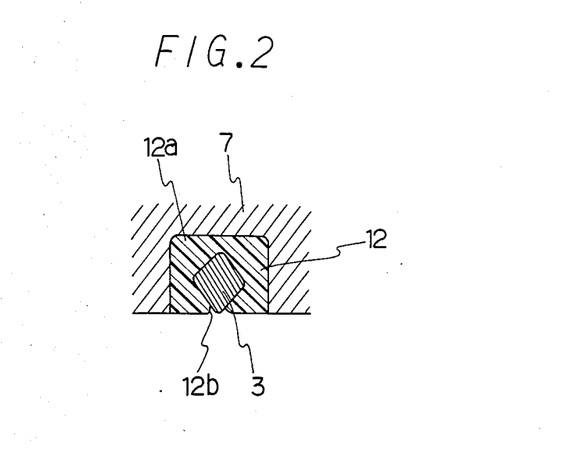
FIG. 2 is a sectional view taken along a line A—A in FIG. 1.

FIGS. 1 and 2 show a first embodiment (an improved Dalbo attachment) of an attachment for a dental prosthesis of the present invention. Numeral 1 indicates a male member of the attachment. The male member 1 has a rail 2, an arm 3 extending from a lower end of the rail 2 outwardly substantially perpendicular to the rail 2 and having a diamond section, and a spherical body 4 provided at a free end of the arm 3. The male member 1 is made of a dental alloy such as Au containing Pt. The rail 2, the arm 3 and the spherical body 4 are formed as one body. The male 1 is defined at a side portion (facing to a later described artificial tooth 7) of a retentive tooth 5 which is formed by cutting a surface of a natural tooth and applying a metallic crown to the cut portion of the natural tooth. The male 1 is secured to the metallic crown of the retentive tooth 5 by soldering or casting as one body.

Numeral 6 is a dental prosthesis. The dental prosthesis 6 has artificial teeth 7, a denture base 8 on which the artificial teeth 7 is held and a female member 9. The female member 9 is defined at a side portion of the artificial tooth 7 facing to the side portion of the retentive tooth 5 to which the male member 1 is secured. The female member 9 has a groove 10 formed by upwardly cutting the side portion of the artificial tooth 7 and defining a frame in the cut portion so that the groove 10 can fitly slide on the rail 2. Also, the female member 9 has a intermediate portion 12 inwardly extending from a lower end of the groove 10 so that the arm 3 of the male member 1 can be received when the male member 1 and the female member 9 are engaged with each other. In order to grip the arm 3 having the diamond section, an elastic part 12a is defined at an interior of the intermediate portion 12 by filling the interior with an elastic material except a space having a diamond section corresponding to the section of the arm 3 and a narrow lower part 12b from which the arm 3 is inserted into the space. Further, the female member 9 has a recess portion 11 defined at an end of the intermediate portion 12 opposite to the groove 10. An elastic part 11a are defined at an inner surface of the recess portion 11 by covering the inner surface with an elastic material so as to define a spherical space. In that case, the shape of the spherical space defined by the elastic part 11a approximately corresponds to the shape of the spherical body 4. As shown in FIG. 1, an opening of the spherical space through which the spherical body 4 is inserted is narrowed so that the elastic part 11a defined in the recess portion 11 can grip the spherical body 4. Numeral 13 indicates an elastic lining layer made of an elastic material. The elastic lining layer 13 is provided over an inner surface of the denture base 8. The elastic parts 11a defined at the inner surface of the recess portion 11, the elastic part 12a defined at the interior of the intermediate portion, and the elastic lining layer are formed as one body and made of the same elastic material. The artificial teeth 7 and the denture base 8 are made of a hard polymer material such as a polymethylmethacrylate. The frame of the groove 10 is made of the same material as the male member 1. The elastic lining layer and the elastic parts are made of an elastic material such as thermoplastic urethane elstomer.

In operation of such an attachment for the dental prosthesis, the dental prosthesis is downwardly moved along the rail 2 of the male member 1 in the state that the groove 10 is fitly in contact with the rail 2. Then, the arm 3 and the spherical body 4 of the male member 1 are inserted into the intermediate portion 12 and the recess portion 11, respectively, with a little resistance. Consequently, the elastic parts of intermediate portion 12 and the recess portion 11 grip the arm 3 and the spherical body 4, respectively.

Figure 3:
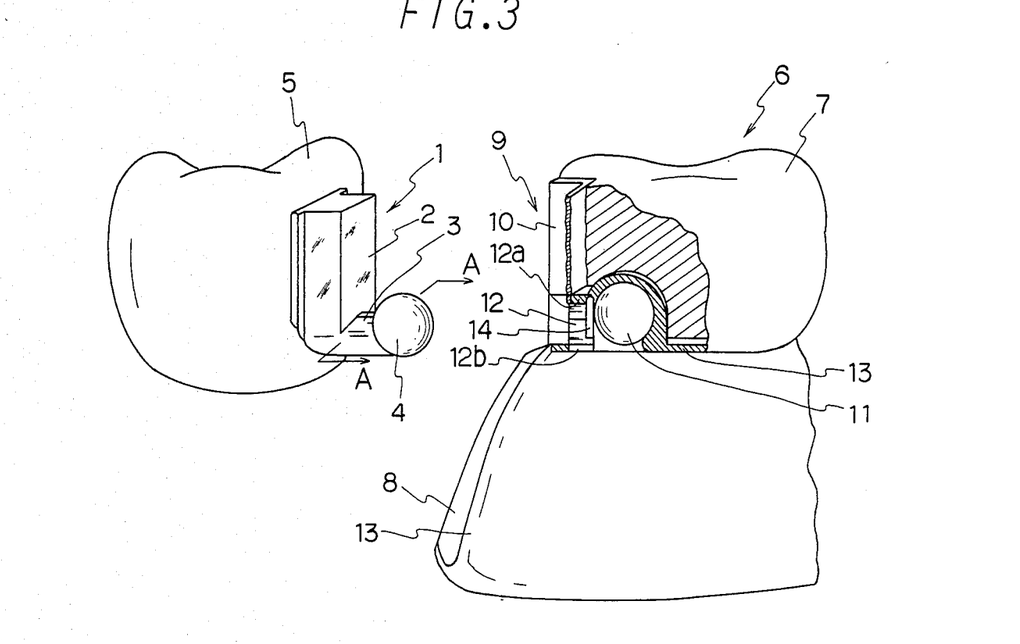
FIG. 3 is a partically cut-away perspective view showing a second embodiment (another improved Dalbo attachment) of the attachment for the dental prosthesis of the present invention.
Figure 4:
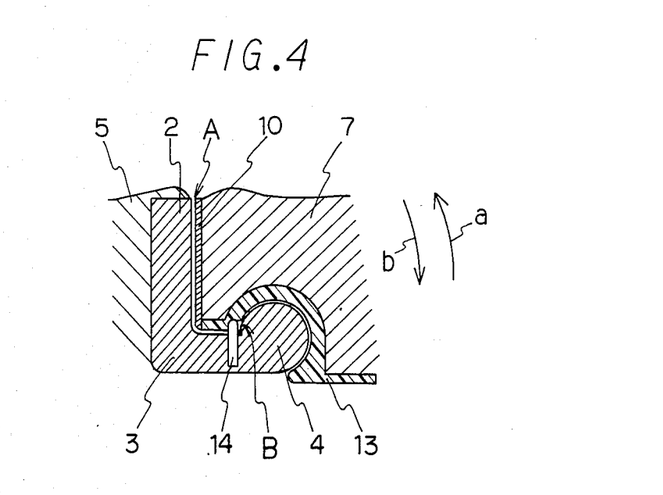
FIG. 4 is a sectional view showing the attachment in the state that a male is engaged with a female.

In FIGS. 3 and 4, a second embodiment (another improved Dalbo attachment) of the attachment for the dental prosthesis is shown. The second embodiment of the attachment is different from the above described first embodiment in the fact that this attachment has a fixing member 14. The fixing member 14 is located at an boundary portion between the recess portion 11 and the intermediate portion 12. The fixing member 14 is an inverse-U-shape member so that the member can straddle the arm 3 of the male member 1 when the male member and the female member are engaged with each other. The fixing member 14 is secured to the artificial teeth 7 or the denture base 8 through a securing part (not shown in the drawings). A small gap having a distance of, for example, about 0.2 mm is provided between the fixing member 14 and the arm 3 so that the fixing member 14 cannot be in contact with the arm 3 when applying an occlusal pressure to the dental prosthesis 6. The fixing member 14 is made of a dental alloy such as Au containing Pt.

When the dental prosthesis having the fixing member 14 is set in a mouth of a patient, the male member 1 and the female member 9 are engaged with each other in the state that the fixing member 14 straddles the arm 3. In FIG. 4, though there exists a small gap between the male member 1 and the female member 9, they are actually in contact with each other closely. During a mastication movement, the dental prosthesis generally sustain a force in the direction of Arrow b, as shown in FIG. 4. On the other hand, when there exists an adhesive matter such as a chewing gum between occlusal surfaces of the upper tooth and the lower tooth facing to each other, the dental prosthesis sustain a force in the direction of Arrow a. When the dental prosthesis sustains a force in the direction of Arrow a, a top end of the groove 10 is pushed to a top end of the rail 2 at A. At the same time, the fixing member 14 is pushed to a surface of the spherical body 4 at B. Therefore, the dental prosthesis is prevented from turning in the direction of Arrow a and coming off from the alveolus ridge. Further, even if the dental prosthesis is centrifugally pulled, the partial dental prosthesis is prevented from coming off from the alveolus ridge, since the fixing member 14 is engaged with the spherical body 4.

In the second embodiment, the fixing member 14 is the reverse-U-shape member, but the fixing member 14 is not limited to the reverse-U-shape member. When the male member 1 is shaped in "J", the fixing member 14 may be a bar-shape member extending from tongue side to cheak side through a portion just above the arm 3 and fixed to the partial dental prosthesis. The bar-shape member has same effects as the reverse-U-shape member.

Figure 5A:
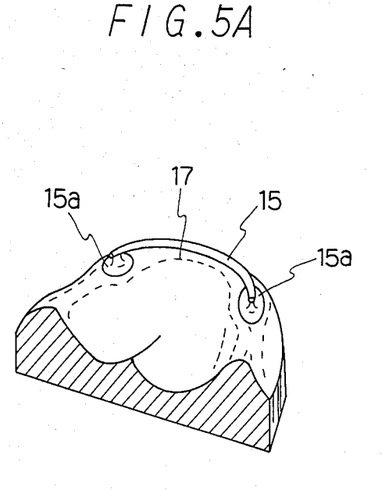
FIGS. 5A and 5B are perspective views showing a third embodiment (an improved bar attachment) of the attachment for the dental prosthesis of the present invention (a male member of the attachment is shown in FIG. 5A and a female member is shown in FIG. 5B)
Figure 5B:
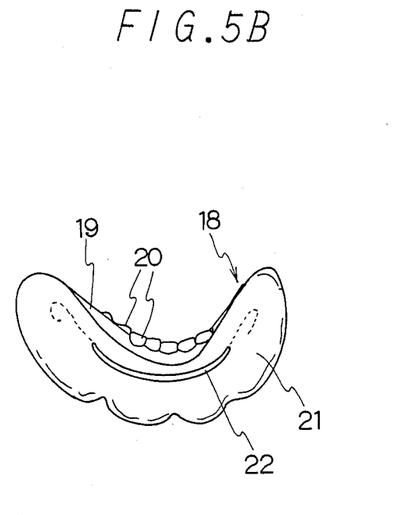
Figure 6:
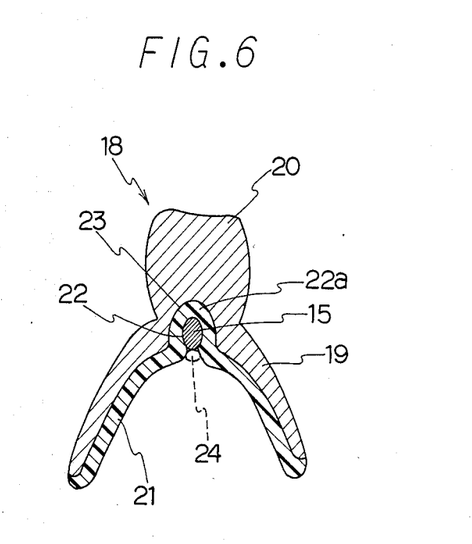
FIG. 6 is a sectional view showing the attachement in FIGS. 5A and 5B in the state that the male member is engaged with the female member.

FIGS. 5A, 5B and 6 show a third embodiment (an improved bar attachment) of the attachment for the dental prosthesis of the present invention. In FIG. 5A, numeral 15 indicates a bar made of a dental alloy such as Au containing Pt and having a section of an approximate circle such as an ellipse. The bar 15 is curved so that the bar 15 extends along an alveolus ridge 17. In general, the length of the bar 15 is approximately equal to the length between both canine teeth along the alveolus ridge 17. The bar 15 have middle members 15a, 15a at both ends which extend in parallel with each other perpendicular to the bar 15. The bar 15 is defined on the alveolus ridge by securing the middle members 15a, 15a to dental roots of natural teeth (for example, canine teeth). In that case, a small distance (about 0.3 to 1.0 mm) exists between the bar 15 and the alveolus ridge 17. In FIG. 5B, numeral 18 indicates a dental prosthesis. The dental prosthesis 18 has artificial teeth 20 and a denture base 19 on which the artificial teeth 20 are held. The artificial teeth 20 and the denture base 19 are made of a hard polymer material such as polymethylmethacrylate. Numeral 21 indicates an elastic lining layer made of an elastic material such as thermoplastic urethane elastomer. The elastic lining layer 21 (about 0.5 mm in thickness) is defined on an inner surface of the denture base 19. Numeral 22 indicates a groove defined in an inner portion of the elastic lining layer 21. The position of the groove 22 corresponds to the position of the bar. The groove 22 is curved correspondingly to the bar 15, and the length of the groove 22 is approximately equal to the length of the bar 15. In FIG. 6, numeral 23 indicates a recess portion provided in an inner surface of the denture base. The position of the recess portion 23 corresponds to the position of the groove 22. An elastic part 22a made of an elastic material and having a required thickness is provided over an inner surface of the recess portion 23 so that the above described groove 22 is defined within the recess porion 23. In that case, the inner shape of groove 22 corresponds to the shape of the bar 15. An opening of the groove 22 through which the bar 15 is inserted is narrowed so that the elastic part 22a can grip the bar 15, as shown in FIG. 6.

In operation of such an attachment for the dental prosthesis, the dental prosthesis 18 is set on the alveolus ridge 17 so that the bar 15 can be engaged with the elastic part 22a. In that case, the bar 15 is gripped by the elastic part 22a, since the above opening of the groove 22 is narrowed. Further, even if the bar 15 and the elastic part 22a are pushed to each other when the dental prosthesis 18 is pressed to the alveolus ridge 17 due to a mastrication movement, the elastic part 22a can absorb the pushing force by elastically deforming like a cushion. When a force which is generated in the horizontal direction or in the rotational direction around an axis extending from tongue side to cheak side is applied to the dental prosthesis, the elastic part 22a can also absorb the force.

The material of the elastic lining layer 21 may be equal to the material of the elastic part 22a defined in the recess portion 23.

The elastic lining layer 21 and the elastic part 22a are provided as one body over the inner surface of the denture base 19 and the inner surface of the recess portion 23, respectively, by means of the following procedure. A mouth model of which shape corresponds to the shape of the alveolus ridge 17 is prepared with gypsum. The bar 15 is fixed to the predetermined position of the alveolus ridge of the mouth model. A spacer 24 is defined between the bar 15 and the alveolus ridge of the mouth model. The spacer 24 may be formed as one body with the mouth model. On the other hand, the denture base 19 on which the artificial teeth 20 are arranged in a row and of which the inner surface is provided with the recess portion 23 is previously prepared. The denture base and the artificial teeth are made of polymethylmethacrylate. Then, the other model in which the denture base 19 is embedded in the state that the inner surface of the denture base is directed outwardly are prepared with gypsum. The models are piled up with each other so that space for the elastic lining layer 21 and the elastic part 22a can be defined. Under the condition, molten thermoplastic urethane elastomer is pored into the space and solidified in order to form the elastic lining layer 21 and elastic part 22a.

In the above embodiment, the elastic part 22a and the elastic lining layer 21 are formed as one body. However, the elastic part 22a can be applied to the dental prosthesis not having the elastic lining layer, namely, only the recess portion 23 may be covered with the elastic material.

Figure 7A:
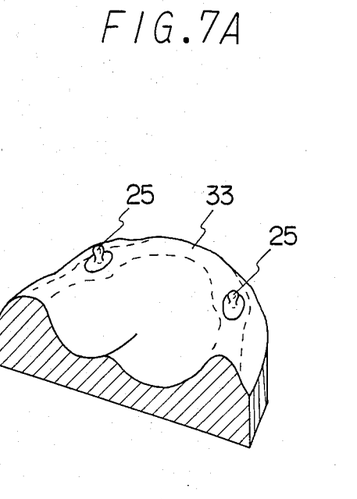
FIGS. 7A and 7B are perspective views showing a fourth embodiment (an improved stud attachment) of the attachment for the dental prosthesis of the present invention (a male member of the attachment is shown in FIG. 7A and a female member is shown in FIG. 7B)
Figure 7B:
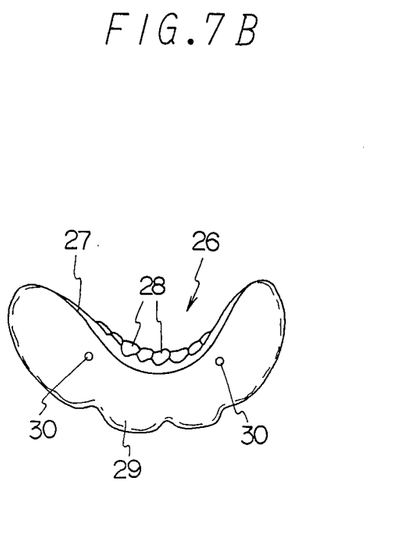
Figure 8:
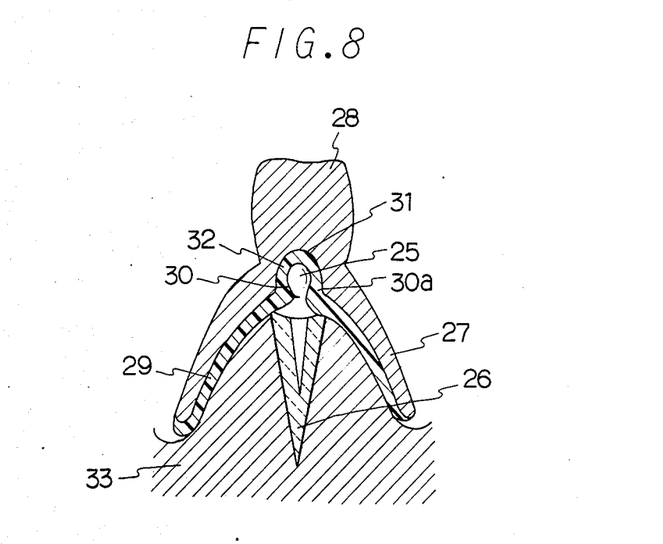
FIG. 8 is a sectional view showing the attachment in FIGS. 7A and 7B in the state that the male member is engaged with the female member.

FIGS. 7A, 7B and 8 show a forth embodiment (an improved stud attachment) of the attachment for the dental prosthesis of the present invention. In FIG. 7A, numeral 25 indicates a male pin made of a dental alloy such as Au containing Pt. The male pin 25 has a head portion formed into an approximate spherical body such as an egg shaped body. In general, two male pins 25 are secured to dental roots 26 of natural teeth (for example, canine teeth). In FIG. 7B, numeral 26 indicates a dental prosthesis. The dental prosthesis 26 has artificial teeth 28 and a denture base 27 on which the artificial teeth 28 are held. The artificial teeth 28 and the denture base 27 are made of a hard polymer material such as polymethylmethacrylate. Numeral 29 indicates an elastic lining layer made of an elastic material such as thermoplastic urethane elastomer. The elastic lining layer 29 (about 0.5 mm in thickness) is provided over an inner surface of the denture base 27. Numerals 30, 30 indicate holes defined in the elastic lining layer 29. The position of the hole 30 corresponds to the position of the male pin 25. In FIG. 8, numeral 31 indicates a recess portion provided in an inner surface of the denture base 27. The position of the recess portion 31 corresponds to the position of the hole 30. An elastic part 30a made of an elastic material and having a required thickness is provided over an inner surface of the recess portion 31 so that the hole 30 is defined within the recess portion 31. In that case, the inner shape of hole 30 corresponds to the shape of the head portion of the male pin 25. The elastic lining layer 29 and the elastic part 30a are formed as one body. An opening of the hole 30 through which the male pin 25 is inserted is narrowed so that the elastic part 30a can grip the male pins 25.

In operation of such an attachment for the dental prosthesis, the dental prosthesis 26 is set on the alveolus ridge 33 so that the male pin 25 can be engaged with the elastic part 30a. In that case, the male pin 25 is gripped by the elastic part 30a, since the opening of the hole 30 is narrowed. Further, even if the male pin 25 and the elastic part 30a are strongly pushed to each other when the dental prosthesis is pressed to the alveolus ridge 33 due to a mastication movement, the elastic part 30a can absorb the pushing force. That is to say, when the male pin 25 and the hole 30 are pushed to each other, the elastic part 30a is elastically deformed like a cushion. Even if a force which is generated in the horizontal direction or in the rotational direction around an axis extending from tongue side to cheak side is applied to the dental prosthesis, the elastic part 30a can absorb the force.

The material of the elastic lining layer 29 may be equal to the material of the elastic part 30a defined in the recess portion 31.

The elastic lining layer 29 and the elastic part 30a are defined on the inner surface of the denture base 27 and the inner surface of the recess portion 31, respectively, by means of the following procedure. A mouth model of which shape is similar to the shape of the alveolus ridge 33 is prepared with gypsum. The male pins 25 are secured to the predetermined positions of the alveolus ridge of the mouth model. On the other hand, the denture base 27 on which the artificial teeth 28 are arranged in a row and of which the inner surface is provided with the recess porion 31 is previously prepared. Then, the other model in which the denture base 27 is embedded in the state that the inner surface of the denture base is directed outwardly is prepared with gypsum. The models are piled up with each other so that space for the elastic lining layer 29 and the elastic part 30a can be defined. Under the condition, molten thermoplastic urethane elastomer is pored into the space and solidified in order to form the elastic lining layer 29 and the elastic part 30a.

In the above embodiment, the elastic part 30a and the elastic lining layer 29 are formed as one body. However, the elastic part 30a can be applied to the dental prosthesis not having the elastic lining layer 29, namely, only the recess portion 31 may be covered with the elastic material.

In the present invention, the hardness of the elastic lining layer and the elastic part can be determined in dependence on various cases in a range of 50 to 80 in JIS A hardness.

In the present invention, it is preferable to employ a thermosetting or crosslinkable polymer as a material of the denture base, and a thermoplastic elastomer as the elastic lining layer and elastic part.

When using the materials of different kinds, it should be noted that the elastic lining layer is readily peeled off from the denture base unless the fixing between them is enough.

According to the present invention, strong fixing can be accomplished by using materials having substantially the same value of solubility parameter value (hereinafter reffered to as "SP value"). The words "materials having substantially the same SP value" means that an SP value of one material is within a range from 85 to 115% of the SP value of the other material.

When the SP values of two polymer materials are substantially the same, the two polymer materials can be readily fused together because of good compatibility therebetween. For instance, when using a thermoplastic urethane elastomer (SP value: 10.0) as the elastic lining layer and the elastic part, it is preferable to employ polymethylmethacrylate (SP value: 9.3 to 9.9) as the denture base and the artificial teeth. Examples of the material for the denture base and the artificial teeth other than polymethylmethacrylate which are compatible with the thermoplastic urethane elastomer are, for instance, polyethersulfone (SP value: 9.7 to 9.9), polysulfone (SP value: 9.7 to 10.7), polycarbonate (SP value: 9.8), and the like.

In the embodiments described above, though the elastic lining layer or the like and the denture base are fixed without any adhesive, the elastic lining layer can also be fixed to the denture base with an adhesive. As the adhesive, it is preferable to employ a solution prepared by dissolving the same polymer material as that of the denture base and/or the elastic lining layer in a solvent having substantially the same SP value as the denture base and/or the elastic lining layer materials. When using polymethylmethacrylate as the denture base material and a thermoplastic urethane elastomer as the elastic lining layer or the like, strong adhesion strength can be obtained by using a solution of polymethylmethacrylate in tetrahydrafran (SP value: 9.9) as the adhesive. Stronger adhesion can be obtained by using a solution of polymethylmethacrylate and thermoplastic urethane elastomer in tetrahydrofuran as the adhesive. In that case, thermoplastic urethane elastomer of the solution is melt and bonded with molten thermoplastic urethane elastomer to be pored. Examples of the solvent, for the adhessive of polymethylmethacrylate are, for instance, n-methylpyrrolidone (SP: 9.8), cyclohexane (SP: 9.9) methylethylkelone (SP: 9.3), diethylketone (SP: 8.8), acetone (SP: 10.0), ethylacetate (SP: 9.1).

In case that Au containing Pt; Ag; a non-noble metallic alloy such as Ni-Co-Cr alloy, or the like is employed as the material of the artificial tooth, a solution containing thermoplastic urethane elastomer and 4-META(4-methacryloxyethyltrimellitic acid anhydride) is preferably employed as an adhesive for the purpose that thermoplastic urethane elastomer is strongly adherred to the artificial tooth made of the metallic alloy.

According to the present invention, the following effects can be obtained.

(the improved Dalbo attachments)

(1) There is no fear that the attachment is damaged even if an excessive large force generates between the male member and the female member, since an inner surface of the recess portion to be engaged with the spherical body is covered with an elastic material, i.e. is provided with the elastic part. Therefore, the dental prosthesis can be stably supported on the alveolus ridge for a long period of time.

(2) The dental prosthesis can be more steadily supported on the alveolus ridge and a large force can be absorbed and uniformly applied to the dental prosthesis, since not only the inner surface of the recess portion is covered with the elastic material so as to grip the spherical body, but also the interior of the intermediate portion is filled with an elastic material except the space having the diamond section so as to grip the arm. Therefore, the life span of the retentive tooth is lengthened.

(3) The dental prosthesis is softly supported on the alveolus ridge and, therefore, an uncomfortable tenderness occurring when an excessive large force is applied to the dental prosthesis can be reduced.

(4) The elastic parts (defined in the recess portion and the intermediate portion) and the elastic lining layer can be formed as one body at a time by molding. Therefore, the manufacturing time can be much shortened in comparison with the conventional manufacturing time. Further, the manufacturing work does not require high technique and high skill which are required in the conventional manufacturing work.

(5) A gap between the female and the denture base does not exist, and therefore, this portion can be sanitarily maintained for a long time in comparison with the conventional attachment.

(6) Conventionally, dregs in the mouth tend to be lodged between a bottom surface of an arm and an alveolus ridge and it is difficult to remove the dregs, since the arm has a square section. However, dregs in the mouth can rarely be lodged between a bottom part of the arm and the alveolus ridge, since the arm has an approximate diamond section. Further, it is easy to clean this portion in the state that the partial dental prosthesis is come off from the alveolus ridge.

(7) The arm can be smoothly inserted into the space of the intermediate portion and be gripped by the elastic part defining the space, since the arm has an approximate diamond section so that the elastic part has a large thickness at its lower part.

(8) The dental prosthesis is stably supported on the alveolus ridge, since the fixing member prevent the dental prosthesis from coming off from the alvelous ridge when a force is applied to the dental prosthesis in the direction that the dental prosthesis comes off from the alveolus ridge.

(the improved bar attachment)

(1) Conventionally, a space exists between a lower end of the sleeve and a coping. An alveolus gingiva rises and the coping is covered with the alveolus gingiva as time goes on. As a result, when the dental prosthesis sustains an occlusal pressure, a sleeve is pushed to the alveolus gingiva. At the time, a patient feels an uncomfortable tenderness. However, according to the present invention, the elastic part and the elastic lining layer are closely in contact with the coping and, therefore, the alveolus gingiva does not rise and the coping is not covered with it.

(2) It is not necessary to provide a space for absorbing the pressure between the bar and the sleeve, since the elastic part is substituted for the space. Further, it is not necessary to provide spaces between the lower outer surfaces of the sleeve and the corresponding lower inner side surfaces of the groove described above, since the elastic part is substituted for the spaces and, therefore, the sanitation can be maintained for a long time, and it is easy to clean the corresponding part.

(3) The dental prosthesis having the attachment is stably and steadily supported on the alveolus ridge for a long time, since the bar is gripped not by the elastic force generated by the metallic sleeve but by the groove defined by the elastic part made of an elastic material.

(4) The bar and the dental root can be protected even if they sustain an excessive force applied to the dental prosthesis in the horizontal direction or in the rotational direction around the axis extending from tongue side to cheak side, since the elastic part made of an elastic material absorbs the excessive force.

(5) Further, the unexpected pain caused by a large force applied to the dental root can be reduced, and the dental prosthesis can be softly set and stably supported on the alveolus ridge.

(the improved stud attachment)

(1) The male pin is elastically pushed into the hole defined by the elastic part when the occlusal pressure is applied to the dental prosthesis, so that the occlusal pressure can be absorbed by the elastic part. Further, since it is not necessary to provide the conventional space for absorbing the pressure, the cutting lines and the space for widening the opened end of cylindrical body is removed, and therefore, the sanitation is maintained for a long time and it is easy to clean the corresponding part.

(2) Conventionally, a space exists between a lower end of the metallic female member and the coping. An alveolus gingiva rises and the coping is covered with the alveolus gingiva as time goes on. As a result, when the dental prosthesis sustains the occlusal pressure, the female is pushed to the alveolus gingiva. At the time, a patient feels an uncomfortable tenderness. However, acccording to the present invention, the elastic part and the elastic lining layer instead of the female member is in closely contact with the coping, and therefore, the alveolus gingiva does not rise.

(3) The dental prosthesis having the attachment is stably and steadily supported on the alveolus ridge for a long time, since the male pin is gripped not by the elastic force generated by the metallic female member but by the hole defined by the elastic part made of elastic material.

(4) The work for manufacturing the female member can be simplified and the manufacturing cost can be reduced, since the female member made of a thermoplastic elastomer is manufactured by molding.

(5) The male pin and the dental root can be protected even if they sustain an excessive force applied to the dental prosthesis on the horizontal direction or in the rotational direction around the axis extending from tongue side to cheak side, since the elastic part absorbs the excessive force.

(6) Further, the unexpected pain caused by a large force applied to the dental root can be reduced, and the dental prosthesis can be softly and stably supported on the alveolus ridge.

What is claimed is:

1. An attachment for a dental prosthesis comprising:
 (a) a male member of rigid material fixedly attached in the patient's mouth adjacent the area to receive the prosthesis; and
 (b) a female member at the area receiving said prosthesis, said female member facing said male member, said male and female members being in intimate interengaging contact with each other without any gap therebetween:
 said female member having a rubber-like resilient part made of rubber-like material for gripping engaging a portion of said male member, said rubber-like resilient part forming an elastic lining layer on an inner surface of the prosthesis base in contact with the alvelous ridge,
 said male member having a rail, an arm extending outward from a lower end of said rail and a spherical body forming said gripping engaging portion at a free end of said arm, and said female member having a groove formed at a side portion of the dental prosthesis for fittingly sliding on the rail, an intermediate portion in which the arm is received and a recess portion having an elastic part defining a spherical space for gripping the spherical body.

2. The attachment of claim 1, wherein said arm has a diamond section and the intermediate portion of said female member has an elastic part defining a space having a corresponding diamond section for gripping the arm of the male member.

3. The attachment of claim 1, wherein said female member has a keying member adjacent the spherical body and secured to the dental prosthesis.

4. The attachment of claim 3, wherein the arm of said male member has a diamond section.

* * * * *